United States Patent [19]

Benecke

[11] 4,424,202

[45] Jan. 3, 1984

[54] AZELAALDEHYDATES AS PSYCHOTROPIC AGENTS

[75] Inventor: Herman P. Benecke, Columbus, Ohio

[73] Assignee: The Vinoxen Company, Inc., Stamford, Conn.

[21] Appl. No.: 387,637

[22] Filed: Jun. 11, 1982

[51] Int. Cl.³ .................. A61U 27/00; A61U 31/19; A61U 31/22; A61U 31/23; A61U 31/40; A61U 31/44; A61U 31/165; A61U 31/445

[52] U.S. Cl. ................................ 424/10; 424/248.55; 424/263; 424/267; 424/274; 424/311; 424/312; 424/317; 424/324

[58] Field of Search ............ 424/10, 311, 312, 248.55, 424/203, 207, 274, 317, 324

[56] References Cited

PUBLICATIONS

Chem. Abst. vol. 78, 1973 (57689w).

*Primary Examiner*—Stanley J. Friedman
*Attorney, Agent, or Firm*—Millen & White

[57] ABSTRACT

A method for producing a psychotropic response, especially for alleviating the symptoms of alcohol withdrawal, comprises administering to a human or animal subject in need thereof a psychotropically effective non-toxic amount of an azelaaldehydate. A composition for use in the present method is provided.

20 Claims, No Drawings

AZELAALDEHYDATES AS PSYCHOTROPIC AGENTS

BACKGROUND OF THE INVENTION

This invention relates to a method for producing a psychotropic response involving administration of an azelaaldehydate. In a composition of matter aspect, the invention also relates to a pharmaceutical composition suitable for use with the foregoing method.

Azelaic semialdehyde is a known compound, as are its methyl and ethyl esters and its sodium salt. Heretofore, there has been no suggestion that azelaldehydates would be useful as psychotropic agents.

OBJECTS OF THE INVENTION

One object of the present invention is to provide a method for producing a psychotropic response, particularly at least one of an antidepressant, tranquilizing or anticonvulsant response, or alleviation of the symptoms of alcohol intoxication or alcohol or tobacco withdrawal.

Another object of the present invention is to provide a pharmaceutical composition for use in the foregoing method.

Upon further study of the specification and appended claims, further objects and advantages of this invention will become apparent to those skilled in the art.

SUMMARY OF THE INVENTION

In a method aspect, the present invention provides a method for producing a psychotropic response in a human or animal subject, comprising administering to said subject a psychotropically effective non-toxic amount of an azelaaldehydate having the formula $[CHO(CH_2)_7COO]_nR_1$, wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2-6$ and $R_1$ is a lower alkyl or cyclo(lower)alkyl polyol residue; or a pharmaceutically acceptable addition salt thereof.

In a composition aspect, the present invention provides a psychotropic composition comprising a non-toxic amoumt effective for producing a psychotropic response in a human or animal subject of an azelaaldehydate, and a pharmaceutically acceptable carrier.

DETAILED DISCUSSION

The term "azelaaldehydate" as used herein embraces azelaic semialdehyde and/or one or more pharmaceutically acceptable esters thereof and pharmaceutically acceptable addition salts of the acid or esters.

Suitable esters can have the formula $CHO(CH_2)_7COOR_1$, wherein $R_1$ is lower alkyl, cyclo(lower)alkyl, aryl(lower)alkyl, lower alkoxy(lower)alkyl, di(lower)alkylamino(lower)alkyl, cyclic amino(lower)alkyl, alkanoylamino(lower)alkyl, and the like.

Illustrative lower alkyl esters include straight or branched chain $C_{1-6}$ alkyl esters, e.g., methyl, ethyl, propyl, isopropyl, tert-butyl, pentyl, hexyl and the like, preferably methyl or ethyl.

Illustrative cyclo(lower)alkyl esters include $C_{3-6}$ cycloalkylesters, e.g., cyclopropyl, cyclobutyl, cyclopentyl, cyclohexyl and the like.

Illustrative aryl(lower)alkyl esters include phenyl-$C_{1-6}$ alkyl esters, e.g., benzyl, phenylethyl and the like; substituted phenyl-$C_{1-6}$ alkyl esters, e.g. p-tolylmethyl, m-chlorophenethyl, and the like; and heteroaromatic-substituted $C_{1-6}$ alkyl esters, e.g., pyridylmethyl and the like.

Illustrative lower alkoxy(lower)alkyl esters include $C_{1-6}$ alkoxy-substituted $C_{1-6}$ alkyl esters, e.g., methoxymethyl, methoxypropyl, ethoxyethyl and the like.

Illustrative di(lower)alkylamino(lower)alkyl esters include, e.g., dimethylaminoethyl, diethylaminoethyl and the like.

Illustrative cyclic amino(lower)alkyl esters include, e.g., N-pyrrolidinylmethyl, N-morpholinylethyl, N-methyl-3-morpholinylethyl, N-piperidinylethyl, N-ethyl-4-piperidinylethyl and the like.

Illustrative lower alkanoylamino(lower)alkyl esters include, e.g., acetamidoethyl, propionamidoethyl, succinimidoethyl and the like.

Suitable pharmaceutically acceptable esters can also have the formula $[CHO(CH_2)_7COO]_nR_1$, wherein $n=2-6$, and $R_1$ is a lower alkyl or cyclo(lower)alky polyol residue. Such esters include, e.g., di-, tri-, tetra-, penta- and hexaesters of azelaic semialdehyde with an alkyl or cycloalkyl polyol, e.g., a $C_{1-6}$ alkylene glycol, glycerol, pentaerythritol, mannitol, inositol and the like.

The foregoing esters can be prepared by conventional esterification of azelaic semialdehyde, which in turn can be prepared by reductive ozonolysis of oleic acid, e.g., by the procedure of Fischer et al., Ber., 65B, 1467 (1932). Methyl azelaaldehydate can be prepared by reductive ozonolysis of methyl oleate, e.g., according to the process of U.S. Pat. No. 3,322,798. Alternatively, oleic acid can be conventionally esterified with alcohols having the formula $R_1OH$, wherein $R_1$ is as defined herein, and the resultant esters can be reductively ozonized to produce the foregoing esters. The oleic esters can also be prepared by conventional transesterification of, e.g., methyl oleate.

Pharmaceutically acceptable addition salts of azelaic semialdehyde include inorganic or organic base addition salts which possess comparable psychotropic activity to the acid and which are otherwise physiologically compatible. Suitable inorganic bases to form these salts include, e.g., the hydroxides, carbonates, bicarbonates or alkoxides of the alkali metals or alkaline earth metals, e.g., sodium, potassium, magnesium, calcium and the like. Suitable organic bases include the following amines; lower mono-, di-, and trialkylamines, the alkyl radicals of which contain up to three carbon atoms, e.g., methylamine, dimethylamine, trimethylamine, ethylamine, di- and triethylamine, N-methyl-N-ethylamine, and the like; mono-, di- and trialkanolamines, the alkanol radicals of which contain up to three carbon atoms, e.g., mono-, di- and triethanolamine; alkylene-diamines which contain up to six carbon atoms, e.g., hexamethylenediamine; phenylalkylamines, e.g., benzylamine, phenylethylamine and N-methylphenylethylamine; cyclic saturated or unsaturated bases containing up to six carbon atoms, e.g., pyrrolidine, piperidine, morpholine, piperazine and their N-alkyl and N-hydroxyalkyl derivatives, e.g., N-methylmorpholine and N-(2-hydroxyethyl)-piperidine, as well as pyridine.

Furthermore, there may be mentioned the corresponding quaternary salts, e.g., the tetraalkyl, e.g., tetramethyl, alkylalkanol, e.g., methyltrimethanol and trimethylmonoethanol, and cyclic ammonium salts, e.g., the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve azelaic semialdehyde in water containing at least one equivalent amount of a hydroxide, carbonate, or bicarbonate corresponding to the inorganic salt desired. Advantageously, the reaction is performed in a water-miscible, inert organic solvent for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, e.g., a lower alkanol, e.g., butanol, or a lower alkanone, e.g., ethyl methyl ketone, gives the solid inorganic salt if that form is desired.

To produce an amine salt, the acid is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or evaporation. If the amine is relatively volatile, any excess can easily be removed by evaporation. It is preferred to use substantially equivalent amounts of the less volatile amines.

Salts wherein the cation is quaternary ammonium are produced by mixing the acid with an equivalent amount of the corresponding quaternary ammonium hydroxide in water solution, followed by evaporation of the water.

Pharmaceutically acceptable addition salts also include salts of basic azelaaldehydate esters with physiologically compatible inorganic or organic acids. Such salts will generally possess comparable pharmacological activity to the corresponding esters, although it may be advantageous to administer the salts rather than the esters for some purposes. The acid addition salts are prepared by reacting a basic ester, e.g., a dialkylaminoalkyl azelaaldehydate or a cyclic aminoalkyl azelaaldehydate, with one or more equivalents, preferably with an excess, of the appropriate acid in an organic solvent, e.g., diethyl ether or an ethanol/diethyl ether mixture.

Suitable acids to form these salts include the common mineral acids, e.g., hydrohalic, sulfuric or phosphoric acid; as well as the organic acids, e.g., formic acetic, maleic, malic, ascorbic, succinic, fumaric, citric, or tartaric acid; or acids which are sparingly soluble in body fluids and which impart slow-release properties to their respective salts, e.g., pamoic or tannic acid or carboxymethylcellulose.

Also included in this invention are the stereoisomers of the foregoing compounds which result from asymmetric centers contained therein. It is to be understood that the diastereomers arising from such asymmetry are included within the scope of this invention. Such diastereomers are obtained in substantially pure form by classical separation techniques and by sterically controlled synthesis.

Individual enantiomers, which might be separated by fractional crystallization of the diastereomeric salts thereof, are also included.

The foregoing examples of pharmaceutically acceptable esters and salts are intended to be illustrative of the scope of the invention, but not limitative thereof, and the invention includes equivalents of the illustrated compounds that also achieve the disclosed psychotropic response.

Illustrative examples of specific compounds which can be used in the method and composition of this invention include azelaic semialdehyde, methyl azelaaldehydate, ethyl azelaaldehydate, n-propyl azelaaldehydate, isopropyl azelaaldehydate, tert-butyl azelaaldehydate, benzyl azelaaldehydate, phenethyl azelaaldehydate, pyridylmethyl azelaaldehydate, diethylaminoethyl azelaaldehydate, 1-pyrrolidinoethyl azelaaldehydate, sodium azelaaldehydate, ammonium azelaaldehydate, piperidinium azelaaldehydate, diethylaminoethyl azelaaldehydate hydrochloride, 1-morpholinoethyl azelaaldehydate succinate, 1,2-propylene glycol bis-azelaaldehydate, glycerol tris-azelaaldehydate, pentaerythritol tetrakis-azelaaldehydate and inositol hexakis-azelaaldehydate. Especially preferred compounds are methyl azelaaldehydate, ethyl azelaaldehydate, sodium azelaaldehydate and azelaic semialdehyde.

It will be appreciated that mixtures of the foregoing azelaaldehydates can also be employed in the method and composition of the invention.

Azelaaldehydates have now been found to possess psychotropic activity, i.e., administration of appopriate dosages to a human or animal subject elicits a psychotropic response. By psychotropic response is meant any one of a variety of therapeutic effects on the central nervous system, which include but are not limited to tranquilizing, antidepressant or anticonvulsant effects, as well as alleviation of the symptoms of alcohol intoxication and/or alcohol or tobacco withdrawal. A preferred method of use is in alleviating alcohol intoxication or withdrawal symptoms, wherein administration of azelaaldehydate is particularly effective.

While the reasons for the effectiveness of any psychotropic agent are oten unclear, it has been found that administration of an azelaaldehydate to humans and animals has a calming, anxiety-reducing effect which is especially helpful for those who are experiencing alcohol or tobacco withdrawal symptoms. In addition, other symptoms associated with alcohol withdrawal are reduced in severity upon administration of an effective amount of an azelaaldehydate in an appropriate dosgae form.

Evaluation of the efficacy of azelaaldehydates in alleviating alcohol withdrawal symptoms is shown by the use of a reliable primate model system, wherein a Cynomolgus monkey is addicted to alcohol over a period of a few weeks, the alcohol is withdrawn and the presence and severity of specific symptoms associated with withdrawal are first evaluated during administration of a placebo, after which the animal is re-addicted to alcohol and the same symptoms are evaluated while an azelaaldehydate is administered during a withdrawal period of the same duration. A comparison of the total symptom score between the placebo withdrawal and the drug withdrawl period is a reliable measure of the efficacy of a drug in alleviating withdrawal symptoms, as disclosed in U.S. Ser. No. 106,129, filed Dec. 21, 1979. In that application, the primate model was used to evaluate a drug which was also clinically tested in a large number of subjects, and the primate model was shown to give results which were consistent with the clinical results.

Administration of an azelaaldehydate for the purpose of eliciting a psychotic response is advantageously effected in daily amounts of about 0.1–150 mg per kg of patient body weight, preferably about 1–50 mg/kg. For the particular purpose of alleviating alcohol withdrawing symptoms, the daily dosage range is about 0.1–20 mg/kg, preferably about 0.5–10 mg/kg. The dose can be administered singly or as divided dosages throughout the day.

Administration of an azelaaldehydate in appropriate dosages to a human or animal, especially a mammal, suffering from nervousness and/or anxiety produces a calming, tranquilizing response. An effective daily tranquilizing dosage of an azelaaldehydate can generally range from about 10 mg to about 3 g, depending on the person or animal treated, the severity of the symptoms and the azelaaldehydate selected.

Administration of an azelaaldehydate in appropriate dosages to a human or animal, especially a mammal, suffering from convulsions produces an anticonvulsant response. An effective daily anticonvulsant dosage of an azelaaldehydate can generally range from about 10 mg to about 3 g, depending on the person or animal treated, the severity of the symptoms and the azelaaldehydate selected.

Administration of an azelaaldehydate in appropriate dosages to a human or animal, especially a mammal, suffering from depression produces an antidepressant response. An effective daily antidepressant dosage of an azelaaldehydate can generally range from about 10 mg to about 3 g, depending on the person or animal treated, the severity of the symptoms and the azelaaldehydate selected.

Administration of an azelaaldehydate in appropriate dosages to a human suffering from tobacco withdrawal symptoms alleviates the symptoms. An effective daily therapeutic dosage of an azelaaldehydate for alleviation of tobacco withdrawal symptoms can generally range from about 10 mg to about 3 g, depending on the person treated, the severity of the symptoms and the azelaaldehydate selected.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, and the like. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosges.

For enteral application, particularly suitable are tablets, dragees, or capsules having talc and/or a carbohydrate carrier or binder or the like, the carrier preferably being lactose and/or corn starch and/or wheat starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, and the like.

Generally, the compounds of this invention are dispensed in unit dosage form comprising about 1 mg–1 g of a pharmaceutical carrier per each unit dosage and the amount of azelaaldehydate is about 0.5–800 mg.

A preferred mode of administration is by oral administration of tablets and/or capsules containing an azelaaldehydate and one or more inert binders and/or excipients. The individual dosage units are advantageously tablets containing about 20–800 mg of azelaaldehydate.

For a patient suffering from alcohol withdrawal symptoms, it is advantageous for the patient to take one such tablet four times per day for the first three days after withdrawal, desirably when the patient is sober, and to take one tablet two or three times per day for the next four days. Such a dosage is generally sufficient to eliminate or reduce the desire or need for alcohol and to alleviate any withdrawal symptoms which the patient might otherwise suffer. If the desire or need for alcohol recurs, the patient may be given an additional supply of the azelaaldehydate tablets, and directed to take a capsule if he or she feels any desire or need for alcohol or any recurrence of withdrawal symptoms.

A combination of injections and tablets or other oral dosage forms may also be used where indicated. In addition, the foregoing dosage forms may be used to reduce the severity of alcohol intoxication and/or to prevent or minimize alcohol intoxication prior to consumption of alcoholic beverages.

Similar dosage forms may be used for eliciting the broad range of psychotropic responses indicated hereinabove. The particular dosages will generally be within the broad ranges given above, but will vary in relation to the severity of the clinical symptoms and the type of response to be elicited, in a manner which will be familiar to the skilled clinical practitioner.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Tablet Formulation

A tablet suitable for administration according to the method of the invention is prepared as follows. Each dosage unit is designed for administration to a patient weighing about 80 kg, and administration of four such tablets on each of the first three days of alcohol withdrawal and two or three tablets for each of the next four days is envisioned. Suitable variation and dosage as a function of patient weight is indicated.

|  | Weight |
|---|---|
| (a) Methyl azelaaldehydate | 80 g |
| (b) Wheat starch | 11 g |
| (c) Lactose | 30 g |
| (d) Magnesium stearate | 2 g |

A granulation obtained upon mixing lactose with a portion of the starch and granulated starch paste made from the remainder of the starch is dried, screened and mixed with the azelaaldehydate and the magnesium stearate. The mixture is compressed into 1,000 tablets weighing about 123 mg each. It will be understood that a dragee or a capsule may be used in place of a tablet, and it may be prepared by conventional techniques.

EXAMPLE 2

Methyl azelaaldehydate was tested for its efficacy in alleviating alcohol withdrawal symptoms in an alcohol-addicted Cynomolgus monkey, using water as a placebo. For each test, a monkey was addicted to ethyl alcohol by infusion of 5 ml/hr for 28 days of a solution ranging between 15 and 30% ethyl alcohol in normal saline. The ethyl alcohol solution was administered via an indwelling silastic catheter implanted into the jugular vein. The presence of and severity of withdrawal was evaluated according to the presence and severity of specific symptoms, which are known to be exhibited by monkeys upon removal of alcohol in a dependent animal. Evaluation was based on a scale of 0: symptom not present, 1: mild presence of symptom, 2: moderate presence of symptom, and 3: severe presence of symptom. The symptoms evaluated were: generalized tremors, muscle fasciculations, elicited hyperreflexia, spasticity, rigidity, spontaneous hyperreflexia, fright, salivation, mydriasis, retching-vomiting, convulsive poses, convulsions, aggression, nervousness, excitability, and evoked threat.

During the 5-day placebo withdrawal period, which immediately followed the 28-day addiction period, the monkey received in 5 ml of water injected into orange slices. The withdrawal symptoms were evaluated daily during this period. At the conclusion of the placebo withdrawal period, the animal was readdicted to the ethyl alcohol over a 14-day period as described above. This was immediately followed by a 5-day drug withdrawal period. During this period, the animal received a daily dose of 8.9 mg of methyl azelaaldehydate dissolved in 5 ml of triolein and injected into orange slices, and the daily withdrawal symptoms were each evaluated using the above rating system. The lower the score, the less severe the symptoms and the more efficacious the therapeutic effect compared to placebo administration. In two test runs, the total symptoms scores were 46 and 52 for placebo and 20 and 35 for methyl azelaaldehydate, representing reductions (placebo-drug/placebo×100) of 57% and 33%, respectively. A percent reduction higher than 20% is considered significant.

It can be seen from these data that azelaaldehydates have been shown to be effective for alleviation of the symptoms of alcohol withdrawal in a reliable primate model. Azelaaldehydates were most effective in reducing nervousness, aggression, fright, threat and generalized tremors.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions. Contemplated modifications include mono or poly substitution of moieties on the azelaic semialdehyde that will not interfere with its psychotropic activity, either as such or in its ester and/or salt forms. Suitable such substituents would include halogen atoms, lower alkyl, lower alkoxy, hydroxy and the like, which can be introduced by conventional means.

What is claimed is:

1. A method for producing a psychotropic response in a human or animal subject suffering from a condition for which a psychotropic response would be therapeutic, comprising administering to said subject a psychotropically effective non-toxic amount of an azelaaldehydate having the formula $[CHO(CH_2)_7COO]_nR_1$, wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2-6$ and $R_1$ is a lower alkyl or cyclo(lower)alkyl polyol residue; or a pharmaceutically acceptable addition salt thereof.

2. The method of claim 1, wherein said subject is suffering from anxiety and said response is a tranquilizing effect.

3. The method of claim 1, wherein said subject is suffering from depression and said response is an antidepressant effect.

4. The method of claim 1, wherein said subject is suffering from convulsions and said response is an anticonvulsant effect.

5. The method of claim 1, wherein said subject is suffering from symptoms of tobacco withdrawal and said response is alleviation of tobacco withdrawal symptoms.

6. The method of claim 1, wherein said effective amount is about 0.1–150 mg per kg of subject body weight per day.

7. The method of claim 6, wherein said amount is about 1–50 mg/kg/day.

8. The method of claim 1, wherein the azelaaldehydate is administered orally.

9. A method for alleviating symptoms of alcohol withdrawal or alcohol intoxication in a human or animal subject suffering from said symptoms, comprising administering to said subject a non-toxic amount effective to alleviate said symptoms of an azelaaldehydate having the formula $[CHO(CH_2)_7COO]_nR_1$, wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2-6$ and $R_1$ is a lower alkyl or cyclo(lower)alkyl polyol residue; or a pharmaceutically acceptable addition salt thereof.

10. The method of claim 9, wherein said subject is suffering from symptoms of alcohol withdrawal and said response is alleviation of alcohol withdrawal symptoms.

11. The method of claim 9, wherein said subject is suffering from symptoms of alcohol intoxication and said response is alleviation of the symptoms of alcohol intoxication.

12. The method of claim 9, wherein said effective amount is about 0.1–20 mg per kg of subject body weight per day.

13. The method of claim 12, wherein said amount is about 0.5–10 mg/kg.

14. The method of claim 12, wherein the azelaaldehydate is administered orally.

15. The method of claim 9, wherein the azelaaldehydate is methyl azelaaldehydate, ethyl azelaaldehydate, sodium azelaaldehydate or azelaic semialdehyde.

16. The method of claim 9, wherein the azelaaldehydate is methyl azelaaldehydate.

17. A psychotropic composition, consisting essentially of a non-toxic amount effective for producing a psychotropic response in a human or animal subject of an azelaaldehydate having the formula $[CHO(CH_2)_7COO]_nR_1$, wherein $n=1$ and $R_1$ is H, lower alkyl, cyclo(lower)alkyl, aryl(lower)alkyl, lower alkoxy(lower)alkyl, di(lower)alkylamino(lower)alkyl, cyclic amino(lower)alkyl or alkanoylamino(lower)alkyl; or $n=2\text{-}6$ and $R_1$ is a lower alkyl or cyclo(lower)alkyl polyol residue; or a pharmaceutically acceptable addition salt thereof;

and a pharmaceutically acceptable carrier;

wherein said composition is in unit dosage form as a tablet, dragee, capsule, ampoule, suppository or sterile injectable preparation.

18. The composition of claim 17, wherein the azelaaldehydate is methyl azelaaldehydate, ethyl azelaaldehydate, sodium azelaaldehydate or azelaic semialdehyde.

19. The composition of claim 17, wherein the azelaaldehydate is methyl azelaaldehydate.

20. The composition of claim 17, wherein said amount is an amount effective to alleviate symptoms of alcohol withdrawal or alcohol intoxication.

* * * * *